(12) United States Patent
Majkrzak et al.

(10) Patent No.: US 9,180,009 B2
(45) Date of Patent: Nov. 10, 2015

(54) DROOP TESTER APPARATUS AND METHOD

(75) Inventors: Carolyn Majkrzak, Santa Ana, CA (US); Roger Lee, Santa Ana, CA (US); Kshitija Garde, Santa Ana, CA (US); Eric Richardson, Santa Ana, CA (US); Benjamin Wong, Santa Ana, CA (US)

(73) Assignee: Medtronic, Inc., Minneapolis, MN (US)

( * ) Notice: Subject to any disclaimer, the term of this patent is extended or adjusted under 35 U.S.C. 154(b) by 704 days.

(21) Appl. No.: 13/480,743

(22) Filed: May 25, 2012

(65) Prior Publication Data

US 2012/0300063 A1    Nov. 29, 2012

Related U.S. Application Data

(60) Provisional application No. 61/489,834, filed on May 25, 2011.

(51) Int. Cl.
| | |
|---|---|
| *A61F 2/76* | (2006.01) |
| *G01L 1/24* | (2006.01) |
| *G01B 11/02* | (2006.01) |
| *A61F 2/24* | (2006.01) |
| *H04N 7/18* | (2006.01) |

(52) U.S. Cl.
CPC .............. *A61F 2/2472* (2013.01); *G01B 11/02* (2013.01); *G01L 1/24* (2013.01); *H04N 7/18* (2013.01); *A61F 2002/7635* (2013.01)

(58) Field of Classification Search
None
See application file for complete search history.

(56) References Cited

U.S. PATENT DOCUMENTS

| | | | |
|---|---|---|---|
| 5,961,549 A | * | 10/1999 | Nguyen et al. ............... 623/2.12 |
| 6,245,105 B1 | | 6/2001 | Nguyen et al. |
| 6,413,275 B1 | | 7/2002 | Nguyen et al. |
| 6,837,902 B2 | | 1/2005 | Nguyen et al. |

FOREIGN PATENT DOCUMENTS

WO    WO 02/31436    *    4/2002    ............. G01B 11/08

OTHER PUBLICATIONS

Keyence, High-Speed High-Accuracy CCD Micrometer LS-7000 Series, "Breakthrough Technology Optical Micrometer with New LED + CCD Optical System" (2001).*
"Information Guide from Keyence SensorCentral.com Optical Micrometers", http://www.sensorcentral.com/micrometers/micrometer02.php (copyright 2007) (archived Oct. 10, 2008 by www.archive.org. and accessed Jan. 21, 2015).*

* cited by examiner

*Primary Examiner* — William C Vaughn, Jr.
*Assistant Examiner* — Lindsay Uhl (57) ABSTRACT

The invention relates to a system for testing heart valve leaflets. The system includes a leaflet support assembly with a support post for receiving and supporting a leaflet to be tested, the post being disposed in a target region of the support assembly. The system also has a transmitter assembly that includes a light source and is configured and arranged to direct light from the light source onto the target region. The system further includes a receiver assembly that has an image sensor configured and arranged to sense an image of the target region and generate image information indicative of the sensed image, such as leaflet droop.

17 Claims, 9 Drawing Sheets

DROOP TESTER APPARATUS AND METHOD

RELATED APPLICATIONS

This application claims the benefit of U.S. Provisional Patent Application No. 61/489,834, filed May 25, 2011, which is herein incorporated by reference in its entirety.

BACKGROUND

The present disclosure relates generally to apparatuses and methods of screening and selecting leaflets for use in prosthetic heart valves. More particularly, it relates to apparatuses and methods for droop testing leaflets that measures flexural stiffness of the tissue in order to screen leaflets for use in prosthetic heart valves, for example prosthetic aortic transcatheter valves (TCV).

Prosthetic heart valve fabrication, including aortic transcatheter valve (TCV) fabrication, requires leaflets and skirts to be cut in predetermined geometry from animal-derivative tissue (e.g., porcine pericardium) and then sewn together, often as a tri-leaflet valve. Durability and leaflet wear are critical factors in maintaining acceptable performance over the lifetime of the device. A large factor in the durability of a prosthetic tissue heart valve is the processing and selection of the material. For example, there are three main criteria used to select areas of a pericardial sheet used for the leaflets: thickness, stiffness, and surface features. There are existing technologies to perform thickness mapping. There are also existing technologies to measure material extensibility in terms of deflection (along a Z-axis) in response to an applied load. There is a need for technology to evaluate material stiffness in a non-destructive method. There have been studies which indicate good correlation existing between leaflet droop and material extension in response to applied load.

Material extensibility has shown some indications towards affecting leaflet dynamics and stretching over long duration in wear testing. When a leaflet is suspended from a pin or a forceps, it has a tendency to droop in response to gravity. A leaflet having less stiffness is less resistant to drooping/bending forces, and a leaflet having greater stiffness and higher flexural rigidity is more resistant to drooping/bending. Studies have been conducted to correlate the amount of droop to mechanical properties of the material and which correlates well to a percentage strain at physiological loading. The material property (mechanical properties such as UTS, percentage strain, Young's Modulus) of pericardial tissue, for example, is highly variable and non-uniform within the sac. Valves constructed with stiff leaflets combined with droopy leaflets can cause asynchronous valve closure causing regurgitant fractions to increase. With quantitative measurements, leaflets can be matched or classified based on their droop values.

In light of the above, there is a need for a sensitive, reliable, and repeatable measurement apparatus and method to evaluate leaflet droop in a quantitative manner in order to screen leaflets.

SUMMARY OF INVENTION

The present invention features a system for testing heart valve leaflets. The system includes (i) a leaflet support assembly that has a support post for receiving and supporting a leaflet to be tested, the post being disposed in a target region of the support assembly; (ii) a transmitter assembly that includes a light source and is configured and arranged to direct light from the light source onto the target region; and (iii) a receiver assembly including a first image sensor configured and arranged to sense an image of the target region and generate image information indicative of the sensed image, such as leaflet droop.

In one embodiment of the system, the support post is arranged to support a leaflet to be tested in a manner permitting the corresponding opposing tab ends to freely hang downwardly relative to the post due to gravity. Additionally, the support assembly may include a base configured for placement on a flat surface, and a wall projecting from a floor of the base. In a typical implementation of the invention, the post projects from the wall at a location spaced from the floor to define a vertical spacing between the post and the floor sufficient to permit a leaflet to freely hang from the post. The support assembly may further include a distance indicator located along the wall within the target region and immediately below the post.

The transmitter assembly of the system may include a lens arrangement configured to direct light from the sensor onto the target region as a collimated beam of light. The light source may include, for example, a high-intensity GaN green LED.

In certain embodiments, the transmitter assembly is arranged to direct light at a first side of the target region, and the first image sensor is arranged to sense an image of the target region relative to a second side of the target region opposite the first side. Typically, the first image sensor is a high-speed linear CCD configured to sense a shadow image of the target region. The receiver assembly may further include a second image sensor, such as a CMOS image sensor, configured and arranged to sense an image of the target region and generate output information differing from the image information generated by the first image sensor.

The invention also features a method of testing a leaflet having opposing tab ends for use with an implantable heart valve. The method involves the following steps: loading the leaflet onto a support post of a leaflet support assembly, the leaflet being centrally supported by the post and the opposing tab ends freely hanging downwardly from the post due to gravity; directing light onto the loaded leaflet; collecting an image of the illuminated, loaded leaflet; and determining a parameter related to leaflet droop based upon the collected image. Typically, the collected image is a shadow image, and the parameter related to leaflet droop is the distance between opposing tab ends in the shadow image.

DETAILED DESCRIPTION

Figure 1A:
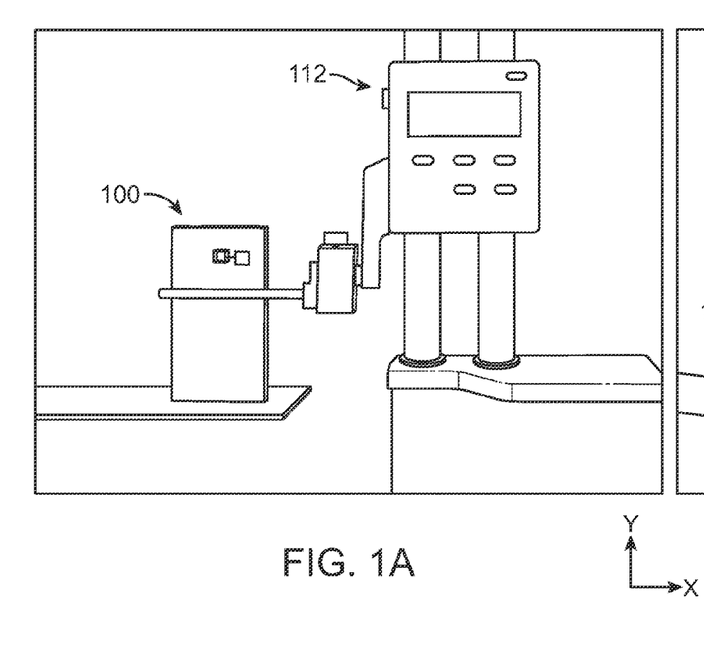
FIGS. 1A and 1B are front and side views of one embodiment of an apparatus in accordance with aspects of the present disclosure.
Figure 1B:
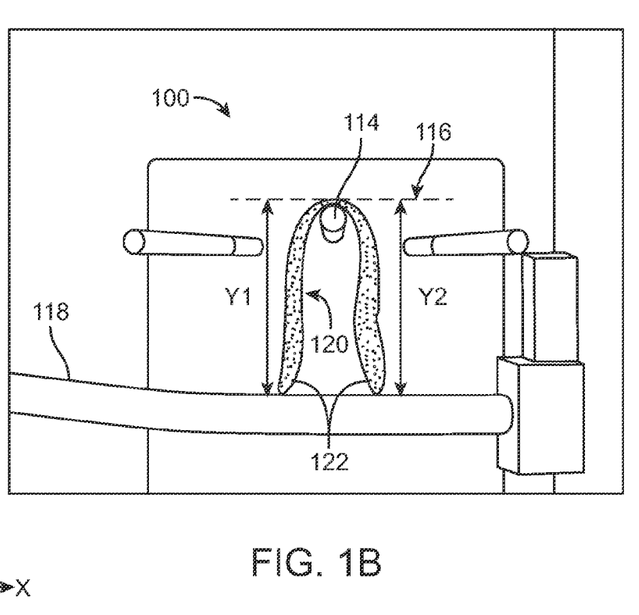

Several embodiments of droop test apparatuses are described herein that are useful for matching or classifying tissue leaflets (e.g., pericardial tissue from different animal origin or polymer) based on droop values in accordance with principles of the present disclosure. One embodiment of a droop test apparatus 100 is illustrated in FIGS. 1A and 1B. The droop testing apparatus 100 includes a gage 112 and a specimen pin 114. The gage 112 can assume various forms appropriate for detecting or measuring height, such as a Mitutoyo Height gage. More particularly, the specimen pin 114 establishes a baseline 116 from which a measurement of an extent of leaflet droop in a "Y" axis direction (labeled in the figures) is gauged. A height probe 118 of the gage 112 is vertically (in the "Y" axis direction) repositionable with respect to the specimen pin 114. During use, a leaflet 120 is positioned over the specimen pin 114, with the specimen pin 114 located at an approximate centerline of leaflet 120 (between opposing tabs 122 of the leaflet 120), and the leaflet 120 is acted upon by gravitational forces. A user causes the probe 118 to move in the Y direction until the leaflet tabs 122 are contacted, generating a distance measurement in the Y direction that is indicative of droop.

Accuracy of droop testing using the droop test apparatus 100 may be subjective or dependent upon an operator/user correctly centering the leaflet 120 on the pin 114, as well as causing or prompting the height gage probe 118 to stop precisely as the height gage probe 118 makes contact with the leaflets tabs 122. The droop tester apparatus 100 may be used to differentiate between visually droopy (greater "Y" distances), stiff (lower "Y" distances), and intermediate (intermediate "Y" distances) of leaflet droop. The user of this method and apparatus 100 has an option to measure the overall "Y" distance if the leaflet 120 is exhibiting similar droop on either side of the specimen pin 114 or take measurements on both sides of the leaflet 120 (e.g. "Y1" and "Y2") in a case of asymmetric droop. It may be difficult for a user of the droop testing apparatus 100 to identify a region within the leaflet tabs 122 that would consistently be used for the measurements. This embodiment of the droop test apparatus 100 may be limited in use because the acceptable range for the "Y" distance between droopy and stiff tissue can be minimal and thus the apparatus 100 may not have sufficient sensitivity for a user wishing to classify tissue to match stiffness. Additionally, the accuracy of the measurements may be dependent on the user.

Figure 2A:
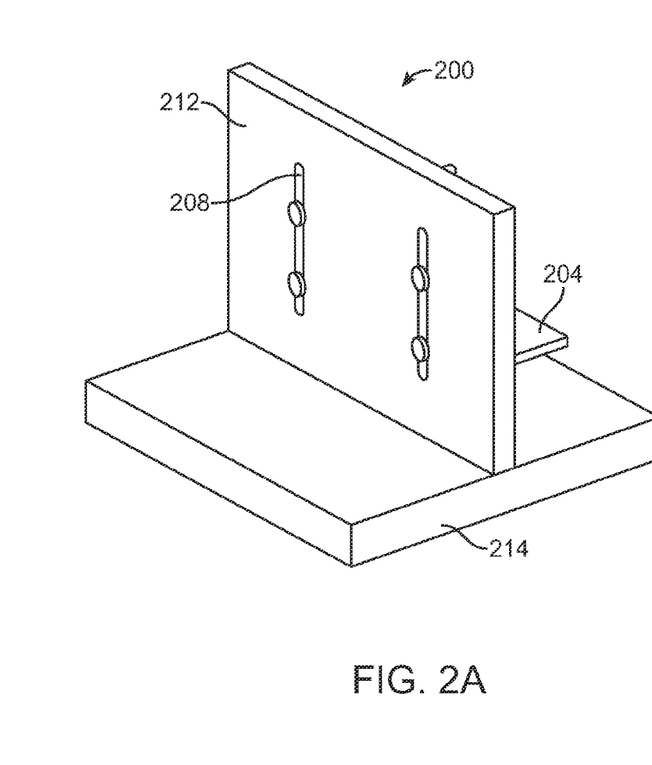
FIGS. 2A and 2B are perspective views of another embodiment of the apparatus in accordance with aspects of the present disclosure.
Figure 2B:
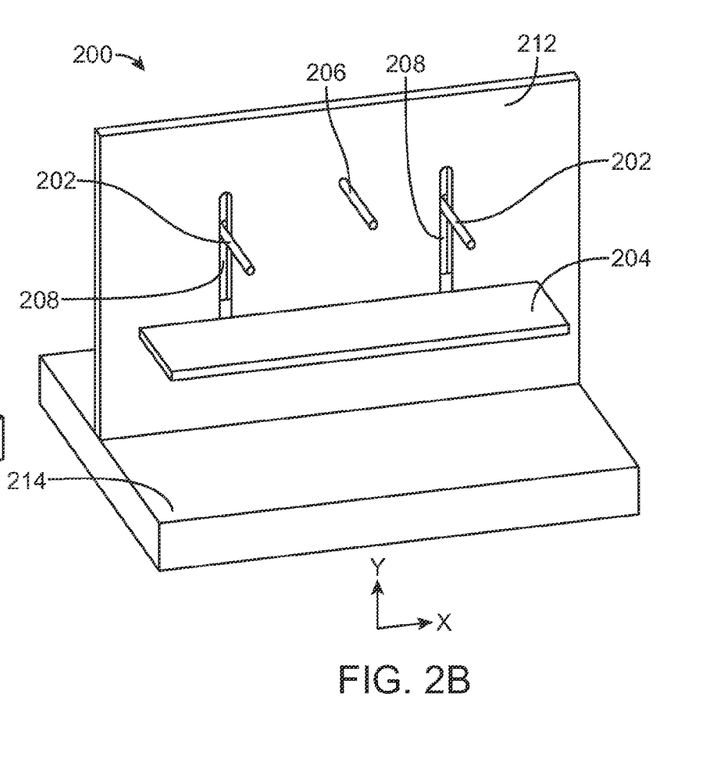

Another embodiment of a droop testing apparatus 200 in accordance with principles of the present disclosure is shown in FIGS. 2A and 2B. In this embodiment, at least two lateral pins 202, a bottom plate 204, and a center pin 206 are connected to a backboard 212 that projects from a base 214 of the droop testing apparatus 200. The center pin 206 is fixedly connected to the backboard 212. The lateral pins 202 and the bottom plate 204 are adjustable to desired positions against which a leaflet (not shown) being tested is designated to either be acceptable or unacceptable. In one embodiment, the lateral pins 202 and the bottom plate 204 are adjustable within slotted connections 208 of the backboard 212. During use of the droop testing apparatus 200, both "X" and "Y" axes of a leaflet are measured against the two lateral pins 202 and the bottom plate 204 when the leaflet is suspended from the center pin 206. With the droop testing apparatus 200, a leaflet with acceptable droop would not contact the laterally placed pins 202 and the bottom plate 204 when the leaflet is suspended from the center pin 206. This embodiment provides a qualitative test by indicating whether the leaflet droop is acceptable or not, but does not provide a quantitative test, and may not directly guide a user in classifying the tested leaflets based on droop values.

Figure 3A:
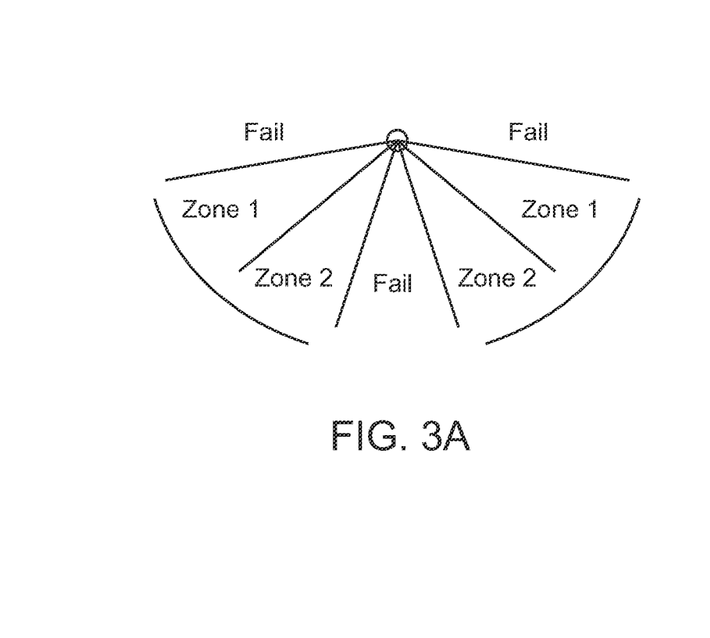
FIGS. 3A through 3D are views of another embodiment of the apparatus in accordance with aspects of the present disclosure.
Figure 3B:
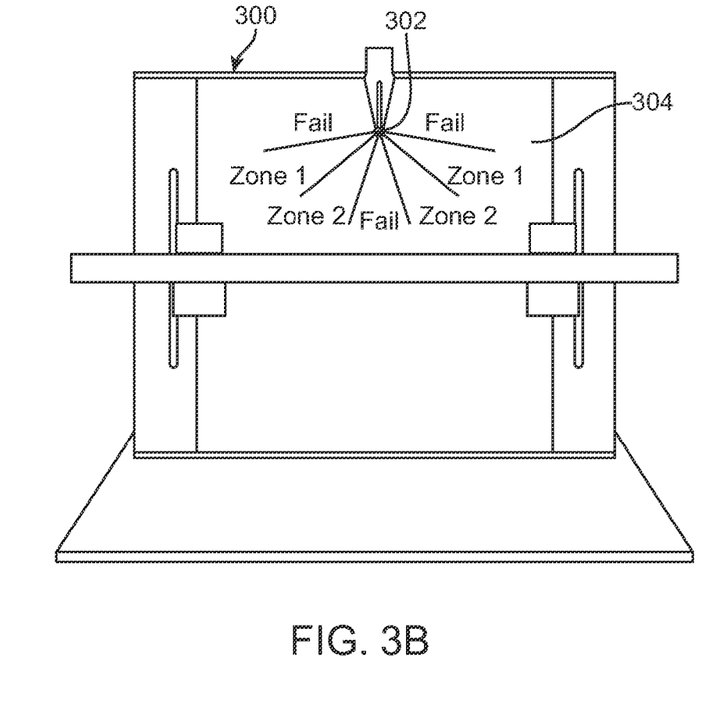

FIGS. 3A-3D illustrate a third embodiment of a droop testing apparatus 300 in accordance with principles of the present disclosure. As illustrated in FIG. 3B, a specimen pin 302 extends perpendicularly from a template 304. With the specimen pin 302 as a center point, the template 304 is divided into and marked as pre-designated ranges within which leaflet tabs 308 (see FIG. 3D) may extend into when positioned over the specimen pin 302. An example of pre-designated ranges, or zones, is illustrated in FIG. 3A which includes Zone 1, Zone 2, and Fail.

Figure 3C:
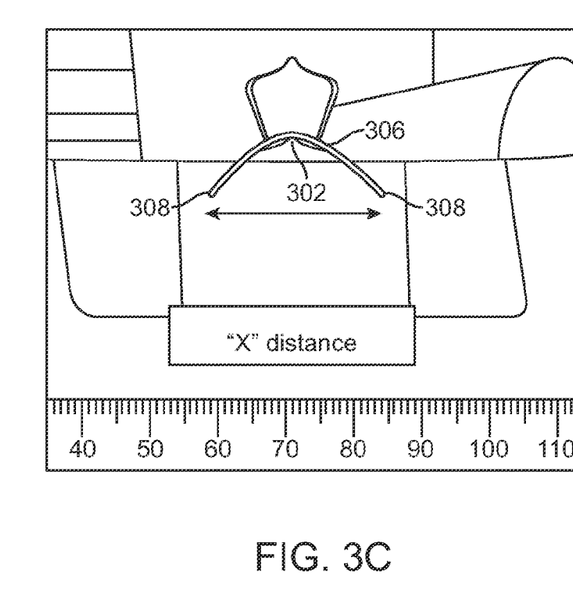
Figure 3D:
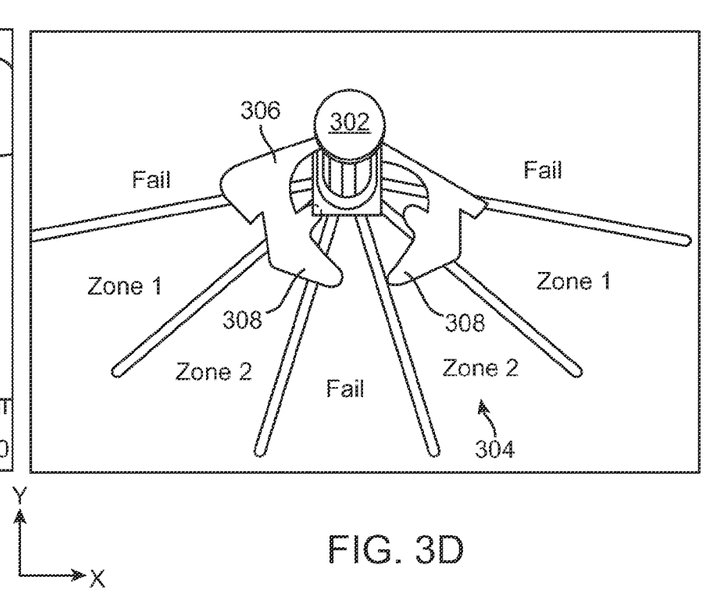

With particular reference to FIGS. 3C and 3D, using the droop testing apparatus 300, a leaflet 306 is suspended on the specimen pin 302 and a photograph is taken by a camera (not shown) positioned in line with the specimen pin 302. Imaging software can be used to measure an "X" axis distance between the leaflet tabs 308, as illustrated in FIG. 3C. Imaging software can also be used to measure the angle between a tangent to a falling edge. A specific region of the leaflet tabs 308 can be selected and tracked to determine which zone the leaflet tabs 308 fall within. In particular, the droop testing apparatus 300 provides a front view analysis of leaflets wherein the leaflets can be classified into categorical groups. For example, the groups may include "Group 1" (where the leaflet tabs lay in Zone 1), "Group 2" (where the leaflet tabs lay in Zone 2), and "Fail".

With the droop testing apparatus 300, imaging measurements require analysis and is retrospective in nature. Thus, this embodiment may be more beneficial in applications other than manufacturing set-up. The accuracy of this method may be dependent on the operator during specimen placement and imaging analysis, camera placement and validity of imaging software. Further, variations in the leaflet tab orientation may prohibit clear projections on captured images, which could make it difficult to identify a specific region that could be used for measurement. Finally, similar to the droop testing apparatus 200 illustrated in FIGS. 2A and 2B, the droop testing apparatus 300 provides a qualitative test by indicating whether the leaflet droop is acceptable or not, but does not provide a quantitative test, as it guides in classifying the leaflets based on leaflet droop categories and not specific droop values.

Figure 4A:
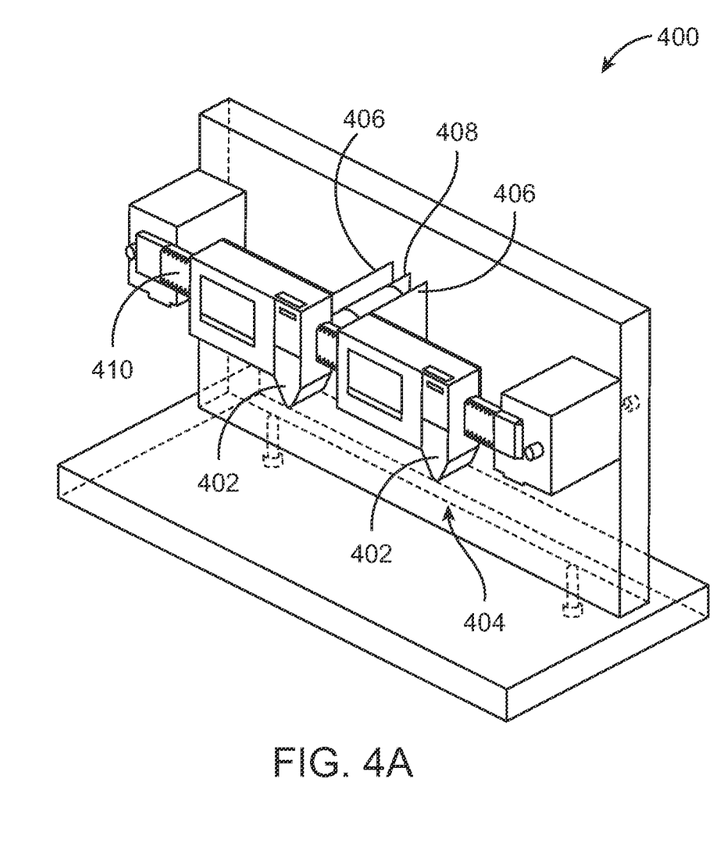
FIGS. 4A and 4B are perspective and side views of another embodiment of the apparatus in accordance with aspects of the present disclosure.
Figure 4B:
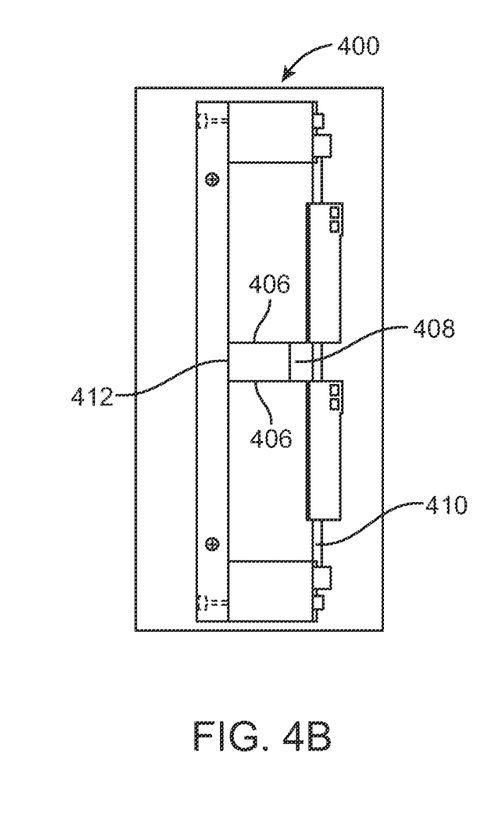

In another embodiment, as illustrated in FIGS. 4A and 4B, droop tester apparatus 400 includes a dual caliper head 402 integrated with a caliper system 404 to form a contact based droop tester. The caliper heads 402 are further connected to stainless steel plates 406 that are moveable along a slider 410 to make contact with the tabs of a leaflet 412 being tested. FIG. 4B is a top view of the droop tester apparatus 400, and illustrates the leaflet 412 positioned over a specimen pin 408 and between the plates 406. In one embodiment, the leaflet droop tester 400 is manually operable instead of automated. The stopping action of the dual caliper head 402 in the droop tester apparatus 400 when it makes contact with the leaflet 412 is operator dependent, thus the accuracy of the measurements may be variable.

Figure 5:
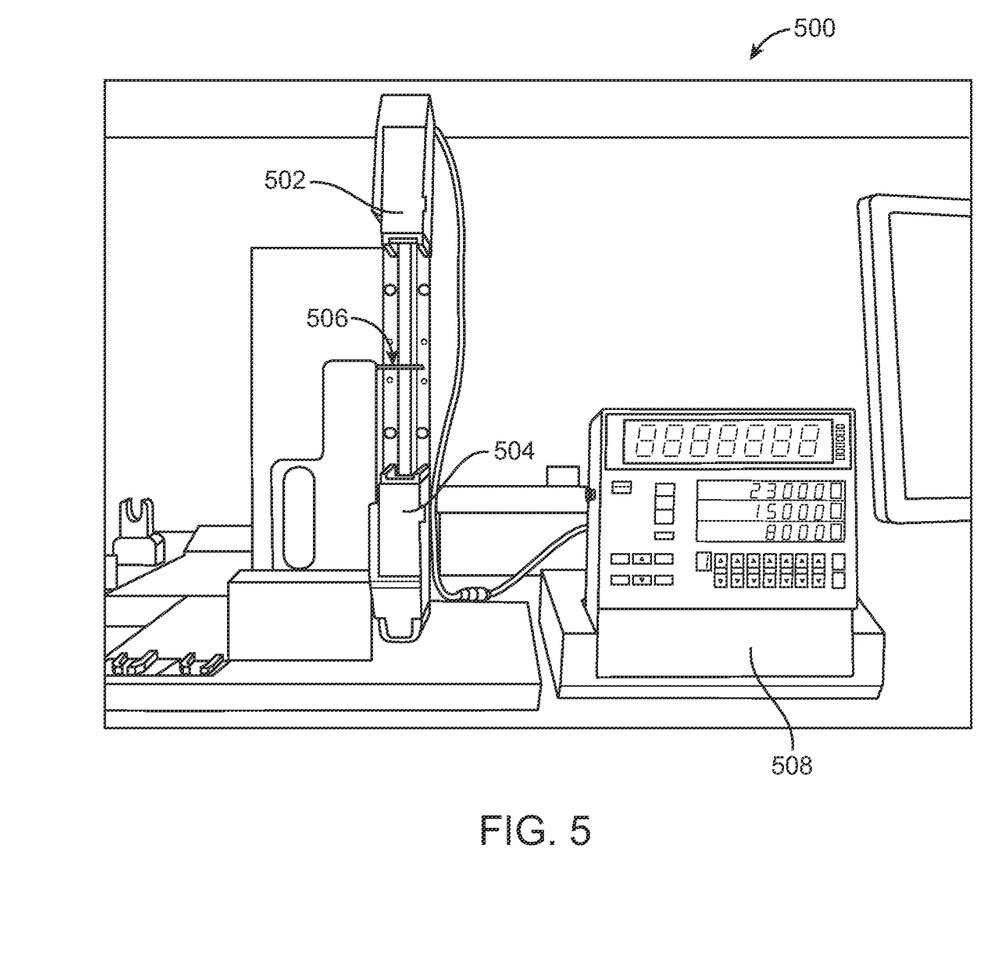
FIG. 5 is a front view of another embodiment of the apparatus in accordance with aspects of the present disclosure.
Figure 6:
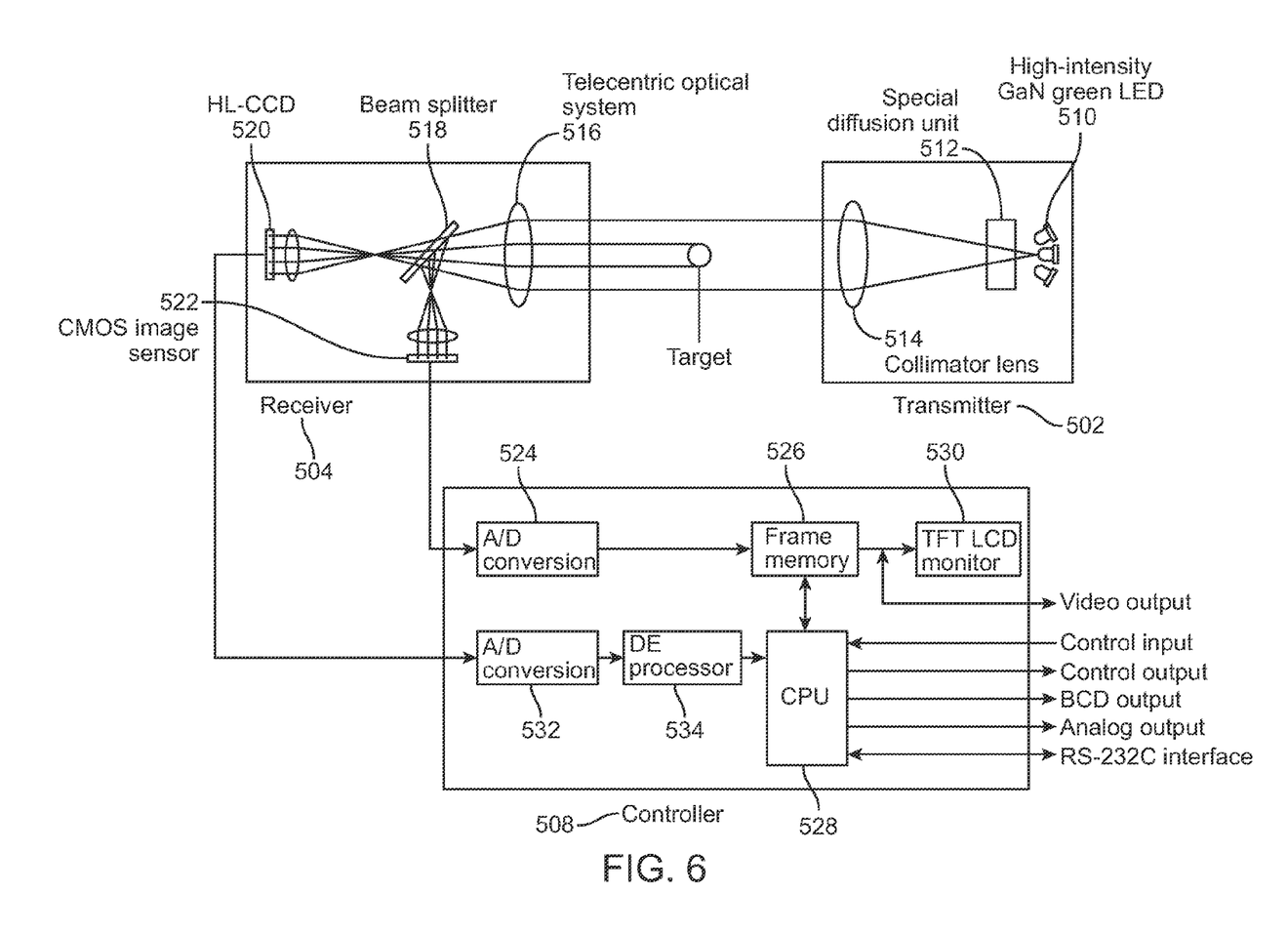
FIG. 6 is a diagram of the droop testing apparatus in accordance with the apparatus of FIG. 5.
Figure 7:
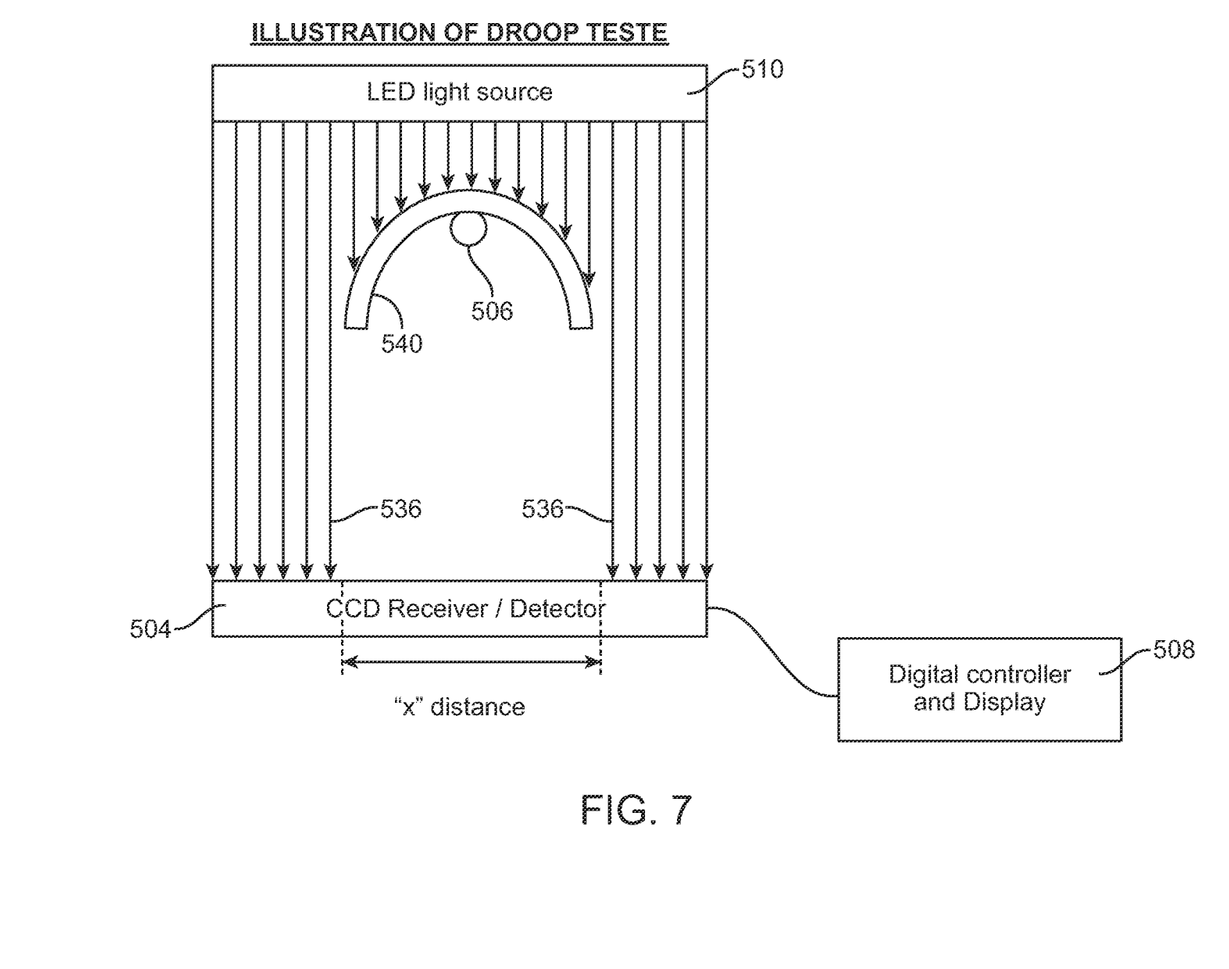
FIG. 7 is a diagram of one aspect of a method of droop testing in accordance with the apparatus of FIG. 5.

Yet another droop tester apparatus 500 and method of use in accordance with principles of the present disclosure are illustrated in FIGS. 5-7. With reference to FIGS. 5 and 6, the droop tester apparatus 500 includes a transmitter 502, a receiver 504, a loading pin 506, and a controller 508. The droop tester apparatus 500 is a non-contact based measurement system. With particular reference to FIG. 6, a light source 510, such as a high-intensity GaN green LED, transmits light through a special diffusion unit 512 and a collimator lens 514 of the transmitter 502. The receiver 504 includes a telecentric optical system 516, a beam splitter 518, a high-speed linear CCD (HL-CCD) 520, and a CMOS image sensor 522. The beam splitter 518 splits an image of a target 540, such as a leaflet, directing one image to the HL-CCD 520 for measurement and another image to the CMOS image sensor 522. In one embodiment, the high-intensity GaN green LED 510 is used along with the HL-CCD 520 in order that dimensions of the target 540 will be displayed and outputed. The image received by the image sensor CMOS 522 is transmitted to a first analog-to-digital (A/D) converter 524 and then to a frame memory 526 of the controller 508. From the frame memory 526, the image data is then transferred to a CPU 528 and a monitor 530 and/or video output for viewing. The image data received by the HL-CCD 520 of the receiver 504 is transmitted to a second A/D converter 532 of the controller 508. The image data is then processed by a digital edge (DE) processor 534 and the CPU 528.

In one embodiment, the droop tester apparatus 500 includes a laser micrometer based measurement system to measure the extent of leaflet droop. With reference to FIG. 7, the light source 510 of the transmitter 502 is emitted onto the target 540. An "X" distance of the shadow image, created by the light source 510 on the target 540, can be detected by the receiver 504. Dimensions of the droop of the target 540 are measured by calculating distance of shadow created by the target 540 on the HL-CCD 520. The extent of the shadow image is detected by finding two edges 536 where light intensity drops using such techniques as digital edge-detection, for example.

Figure 8:
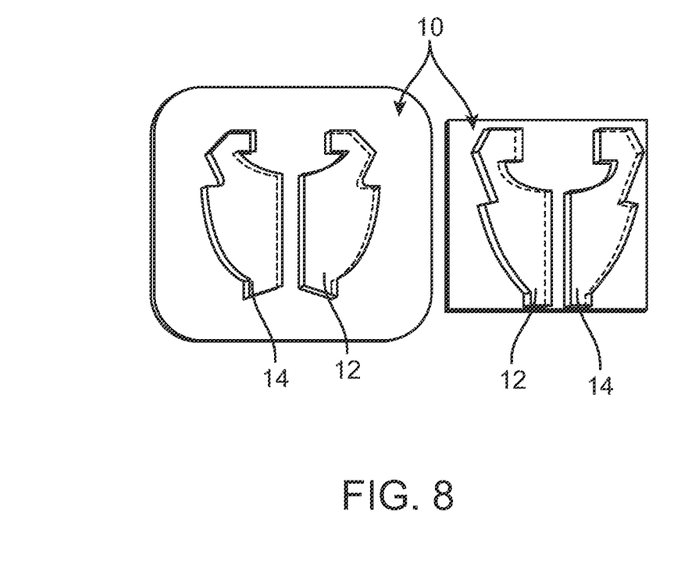
FIG. 8 is a top view of one embodiment of loading template for use with the at least the apparatus of FIG. 5.

FIG. 8 is a top view of two embodiments of loading templates 10 for use with at least the droop testing apparatus 500 of FIGS. 5-7. The loading templates 10 may also be used with the other droop testing apparatuses described above. The loading templates 10 may take a variety of forms corresponding with the desired leaflet tissue sample shape being loaded and tested. An outer contour 12 of the loading templates 10 is geometrically similar to a desired leaflet's boundaries. An indentation 14 is formed to correspond to and accommodate the loading pin 506 of the droop testing apparatus 500, for example. In one embodiment, the loading pin 506, and the associated indentation 14, may be 2 mm in diameter, for example.

Figure 9:
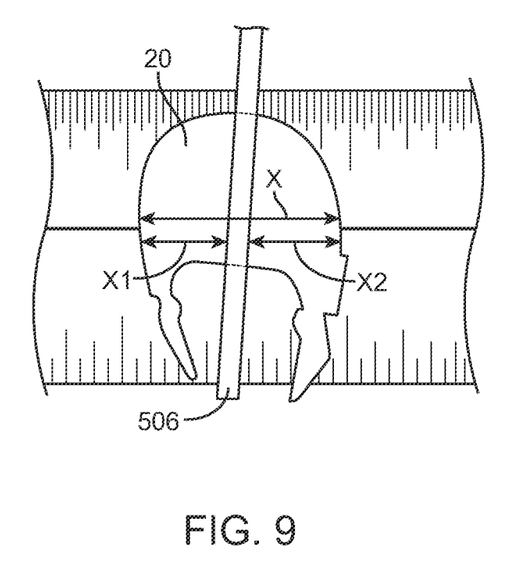
FIG. 9 is a top view of a material sample on the apparatus of FIG. 5.

FIG. 9 is a top view of a tissue sample on the apparatus of FIG. 5. In one embodiment a leaflet 20 is blotted and placed on the loading template 10 of FIG. 8, described above. The leaflet 20 may be placed on the loading template 10 to guide in consistent loading of the leaflet 20 along an axis of symmetry at the centerline of the loading pin 506. The leaflet 20 is then loaded onto the loading pin 506 and a measurement reading may be displayed, as discussed above with respect to FIGS. 5 through 7. As illustrated in FIG. 9, the droop testing apparatus 500 of FIG. 5 may be used to measure the total shadow distance "X" or individual distances on either sides of pin (i.e. "X1" and "X2"). In one embodiment, in order to calculate X1 or X2, the operator has to manually calculate the distance between ends of CCD detector 520 to a mid-point of the loading pin 506 as the droop tester apparatus 500 read out give measurements of the end of the target shadow to the detector edge.

Although the present disclosure has been described with reference to preferred embodiments, workers skilled in the art will recognize that changes can be made in form and detail without departing from the spirit and scope of the present disclosure.

What is claimed is:

1. A system for testing heart valve leaflets, each leaflet defining opposing tab ends, the system comprising:
   a leaflet support assembly including a support post for receiving and supporting a leaflet to be tested, the post being disposed in a target region of the support assembly, wherein the support assembly further includes a base configured for placement on a flat surface, and a wall projecting from a floor of the base, and further wherein the post projects from the wall at a location spaced from the floor to define a vertical spacing between the post and the floor sufficient to permit a leaflet to be tested to freely hang from the post;
   a transmitter assembly including a light source, wherein the transmitter assembly is configured and arranged to direct light from the light source onto the target region; and
   a receiver assembly including a first image sensor configured and arranged to sense an image of the target region and generate image information indicative of the sensed image;
   wherein the image information is indicative of leaflet droop.

2. The system of claim 1, wherein the support post is arranged to support a leaflet to be tested in a manner permitting the corresponding opposing tab ends to freely hang downwardly relative to the post due to gravity.

3. The system of claim 1, wherein the support assembly further includes a distance indicator located along the wall within the target region and immediately below the post.

4. The system of claim 1, wherein the transmitter assembly further includes a lens arrangement configured to direct light from the sensor onto the target region as a collimated beam of light.

5. The system of claim 1 wherein the light source includes a high-intensity GaN green LED.

6. The system of claim 1, wherein the transmitter assembly is arranged to direct light at a first side of the target region, and the first image sensor is arranged to sense an image of the target region relative to a second side of the target region opposite the first side.

7. The system of claim 1, wherein the first image sensor is configured to sense a shadow image of the target region.

8. The system of claim 1, wherein the first image sensor is a high-speed linear CCD.

9. The system of claim 1, wherein the receiver assembly further includes a second image sensor configured and arranged to sense an image of the target region and generate output information differing from the image information generated by the first image sensor.

10. The system of claim 9, wherein the second image sensor is a CMOS image sensor.

11. The system of claim 1, further comprising:
    a controller electronically coupled to the first image sensor and programmed to determine a parameter relating to leaflet droop based upon the image information.

12. The system of claim 11, wherein the first image sensor is configured to generate the image information as being indicative of a shadow image of a leaflet disposed on the post in the target region, and further wherein the controller is programmed to determine a distance between opposing tab ends of the corresponding leaflet based upon the shadow image information.

13. The system of claim 12, wherein the controller is programmed to perform digital edge detection on the shadow image information.

14. The system of claim 1, further comprising:
- a template defining a recess configured to generally arrange a leaflet to be tested about a center point;
- wherein the template is configured to be coupled to the support assembly immediately adjacent the post.

15. A method of testing a leaflet for use with an implantable heart valve, the leaflet defining opposing tab ends, the method comprising:
- loading the leaflet onto a support post of a leaflet support assembly and centering the leaflet over the post, including the leaflet being centrally supported by the post and the opposing tab ends freely hanging downwardly from the post due to gravity;
- directing light onto the loaded leaflet;
- collecting an image of the illuminated, loaded leaflet; and
- determining a parameter related to leaflet droop based upon the collected image.

16. The method of claim 15, wherein the collected image is a shadow image.

17. The method of claim 16, wherein the step of determining a parameter includes determining a distance between opposing tab ends in the shadow image.

* * * * *